United States Patent [19]

Fujioka et al.

[11] Patent Number: 4,900,304
[45] Date of Patent: Feb. 13, 1990

[54] SOLID PREPARATION ADMINISTERING INSTRUMENT

[75] Inventors: Keiji Fujioka, Amagasaki; Shigeji Sato, Ibaraki; Nobuhiko Tamura, Toyonaka; Yoshihiro Takada, Takatsuki; Yoshio Sasaki, Toyonaka, all of Japan

[73] Assignee: Sumitomo Pharmaceuticals Company, Limited, Osaka, Japan

[21] Appl. No.: 79,429

[22] Filed: Jul. 30, 1987

[30] Foreign Application Priority Data

| Jul. 30, 1986 [JP] | Japan | 61-180398 |
| Jul. 30, 1986 [JP] | Japan | 61-180399 |
| Jul. 30, 1986 [JP] | Japan | 61-180400 |

[51] Int. Cl.$^4$ .............................. A61M 5/00
[52] U.S. Cl. ...................... 604/60; 604/242
[58] Field of Search ............ 604/57, 59, 60, 61, 604/62, 64, 891.1, 232, 234, 240, 242; 128/330

[56] References Cited

U.S. PATENT DOCUMENTS

| 2,513,014 | 6/1950 | Fields | 604/60 |
| 2,727,514 | 12/1955 | Lockhart | 604/242 |
| 2,761,446 | 9/1956 | Reed | 604/59 |
| 3,016,895 | 1/1962 | Sein . | |
| 3,744,493 | 7/1973 | Booher et al. | 604/60 |
| 3,786,807 | 1/1974 | Dubin | 604/60 |
| 4,077,406 | 3/1978 | Sandhage et al. | 604/61 |
| 4,086,914 | 5/1978 | Moore | 604/57 |
| 4,154,239 | 5/1979 | Turley | 604/61 |
| 4,245,635 | 1/1981 | Kontos . | |
| 4,402,308 | 9/1983 | Scott . | |
| 4,451,253 | 5/1984 | Harman . | |
| 4,774,091 | 9/1988 | Yamahira et al. | 604/60 |

FOREIGN PATENT DOCUMENTS

| 0139286 | 5/1985 | European Pat. Off. . | |
| 61-79470 | 4/1986 | Japan . | |
| 61-82761 | 4/1986 | Japan . | |
| 252587 | 6/1926 | United Kingdom | 604/60 |
| 821087 | 9/1959 | United Kingdom | 604/62 |

Primary Examiner—Stephen C. Pellegrino
Assistant Examiner—Ralph Lewis
Attorney, Agent, or Firm—Birch, Stewart, Kolasch & Birch

[57] ABSTRACT

An device for administering solid or semisolid preparations under the skin, which comprises a solid needle member with an acute tip end, and a cylindrical member slidably mounted on the needle member. The solid needle member having a recess at its front part to form a preparation chamber between the needle member and cylindrical member, and the chamber being opened or closed by moving the cylindrical member in the direction parallel to the axis of the needle member. The device may comprises a cylindrical member with a capsule chamber, a hollow needle member removable mounted on the front end of the cylindrical member, and a plunger slidably arranged in the capsule chamber of the cylindrical member, all of which have a common axis so that the plunger enters into the hollow needle member through the capsule chamber.

6 Claims, 5 Drawing Sheets

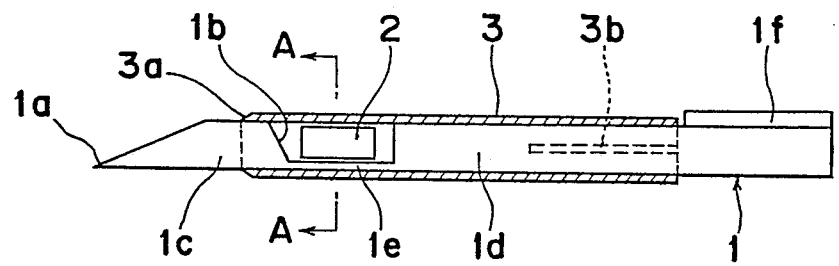
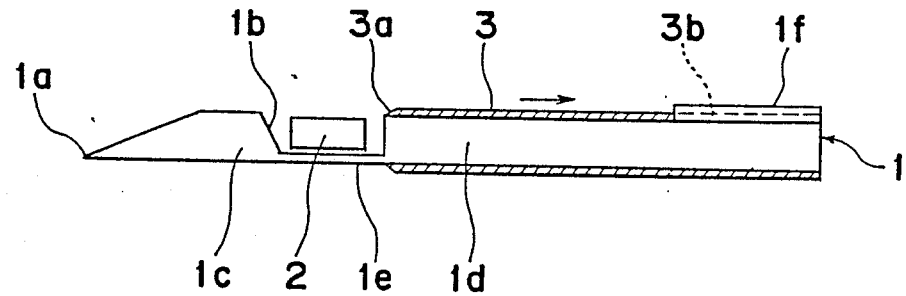
Fig. 2
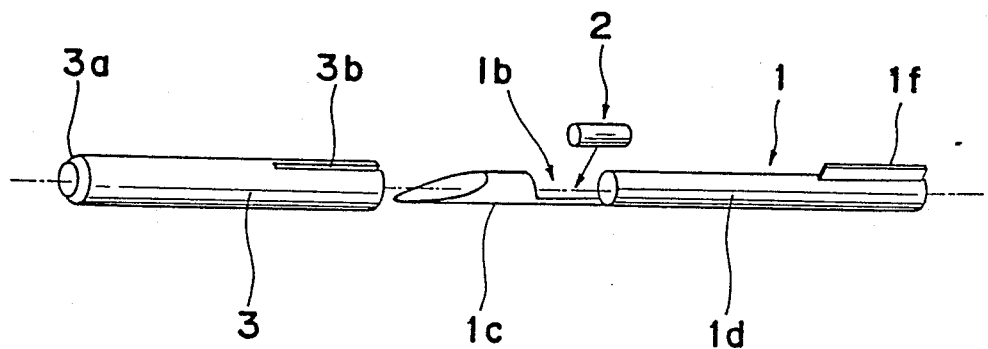
Fig. 3

SOLID PREPARATION ADMINISTERING INSTRUMENT

FIELD OF THE INVENTION

The present invention relates to a solid preparation administering instrument and, more particularly, an instrument for administering solid or semisolid preparations under the skin of a patient.

BACKGROUND OF THE INVENTION

So far there has been known subcutaneous implantation by which one or more solid preparations are administered to the body of a patient to perform medical treatments. In the implantation, however, it is required to perform a surgical operation accompanied with physical and mental sufferings of the patient, thus making it difficult to frequently perform subcutaneous implantation of solid preparations.

To solve such a problem, some of the inventors have proposed use of an instrument for administering solid preparations under the skin, for example, in EP-A-139286, Japanese patent applications laid-open Nos. 61-79470, and 61-82761. The instrument generally comprises a fine tube and a plunger removably mounted therein and is operated in the following manner. Firstly, the plunger is pulled out of the fine tube and, after loading a solid preparation into the fine tube from its rear end, the plunger is inserted again into the fine tube. The solid preparation is then injected into the body by inserting the fine tube into the body and then pushing the plunger.

Such an instrument makes it possible to implant solid preparations under the skin of the body without performing surgical operations, but it has various problems awaiting a solution. For example, the operations are troublesome and take a long time since the plunger must be removed from the fine tube each time when loading the solid preparation into the fine tube. Since the solid preparation is frequently caught by a joint of the fine tube, it is difficult to administer the solid preparations smoothly, thus making it impossible to administer two or more preparations at the same time. Further, the plunger is an elongated fine member, so that the insertion of the plunger into the needle is difficult and requires prudent cares to prevent the plunger from bending or breaking. The longer the fine tube, the greater the force required for the sliding movement of the plunger. In addition, there is a fear that the solid preparation would lose its original form by the friction with the inside wall of the fine tube during movement from the rear end of the fine tube to the front end. The instrument is designed to administer a completely or partially bared solid preparation to the body, thus making it difficult to aseptically handle the solid preparations to be loaded into the instrument.

SUMMARY OF THE INVENTION

It is therefore an object of the present invention to provide a device for administering solid or semisolid preparations, which is easy to handle and simple in construction.

Another, object of the present invention is to provide a device for administering solid or semisolid preparations which makes it possible to inject one or more solid or semisolid preparations into the body at one time with ease.

Still another object of the present invention is to provide a device for administering solid or semisolid preparations which makes it possible to aseptically administer one or more solid or semisolid preparations to the body of a patient.

According to the present invention, these objects are solved by providing a device for administering solid or semisolid preparations, comprising a solid needle member with an acute tip end, and a cylindrical member slidably mounted on the needle member, said needle member having a recess at its front part to form a preparation chamber between the needle member and cylindrical member, said preparation chamber being opened or closed by moving said cylindrical member in the direction parallel to the axis of the needle member.

According to the present invention, there is also provided a device for administering solid or semisolid preparations, said device comprising a cylindrical member with a capsule chamber, a hollow needle member removably mounted on the front end of the cylindrical member, and a plunger slidably arranged in the capsule chamber of the cylindrical member, said needle member and plunger having a common axis so that the plunger enters into the hollow needle member through the chamber.

In a preferred embodiment of the present invention, the above device further comprises a means for forcing the plunger toward the front end of the hollow needle member, and a means for changing the position of a pushing head of the plunger from its resting position close to the rear end of the capsule chamber to its working position close to the tip of the needle member or vice versa.

Preferably, the capsule chamber of the cylindrical member is so designed that two or more capsules are loaded therein in a row along the axis of the cylindrical member.

As a material for the needle member, there may be used for example, stainless steel or any other material which ensures that no interaction takes place between the needle member and solid preparations and has a mechanical strength which can stand the forces applied during insertion and removal of the needle member. The solid needle member 1 is generally designed so as to have a diameter ranging from 0.5 to 3 mm and a length of 30 to 150 mm.

The solid preparations may be encapsulated in protective capsules which comprises a cylindrical capsule body sealed at its opposite ends with sealing films of a biologically compatible material to keep the preparation in aseptic conditions. Preferably, the needle member comprises a hollow fine tube and a fixing member mounted on the rear end of the fine tube to form a stopper for the capsule body. The capsule body has a relatively large outside diameter, preferably, of greater than 3 mm, an inside diameter ranging from 0.5 to 3 mm, and a length ranging from 5 to 50 mm. The capsule body is made of such a material that no interaction occurs between the capsule material and preparations to be encapsulated. As a material for the capsule body, it is preferred to use a transparent material. The transparent materials include, without being limited to, polyethylene, silicone, polypropylene, polytetrafluoroethylene, and other plastics.

In the solid preparation administering device of the present invention, at least one solid or semisolid preparations are loaded into the instrument from its front part and then injected into the body through the hollow needle or opening of the solid needle. Thus, the instrument of the present invention may hereinafter be called "a solid preparation injector".

The solid preparation injector of the present invention is simple in operation and easy to load solid preparations into a preparation chamber. Also, the frontloading contributes to decrease stroke of the plunger, which in turn makes it possible to prevent it from breaking or bending during injection of solid preparations. The short stroke of the plunger makes it possible to prevent the solid preparations from deformation during its sliding movement. The solid preparation injector according to the present invention makes it possible to administer two or more solid preparations to the body at one time.

The present invention will be further apparent from the following description taken in conjunction with the accompanying drawings which show, by way of example only, preferred embodiments thereof.

BRIEF EXPLANATION OF THE DRAWINGS

FIG. 1 is a partially cutaway view of a solid preparation injector embodying the present invention, with a solid preparation being loaded therein;

FIG. 2 is a partially cutaway view of the solid preparation injector of FIG. 1, showing a cylindrical member being slid backwards to administer the solid preparation;

FIG. 3 is an exploded perspective view of the solid preparation injector of FIG. 1;

PREFERRED EMBODIMENT OF THE INVENTION

Figure 4A:
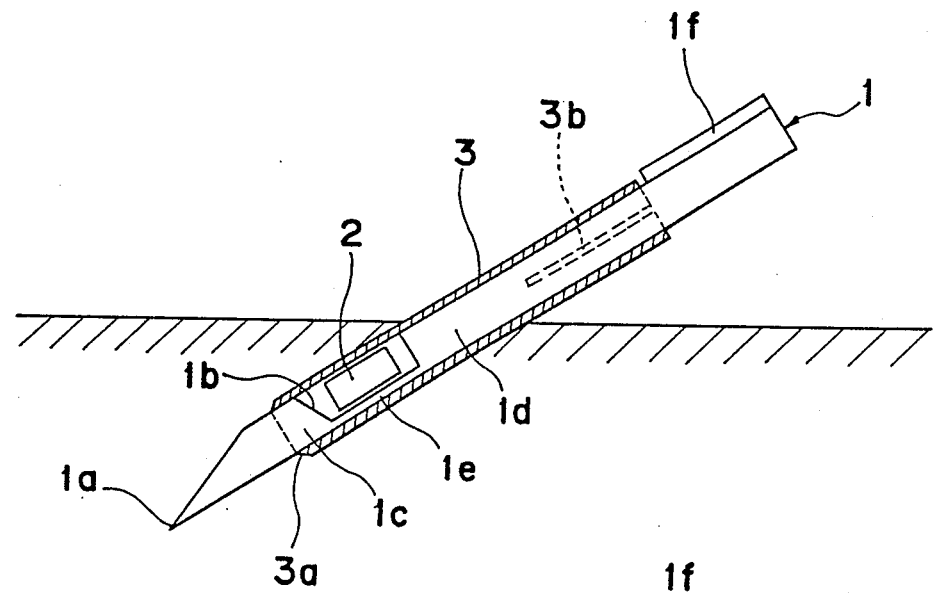
FIGS. 4a and 4b are cross sections illustrating operation of the solid preparation injector of FIG. 1.

Referring now to FIGS. 1 to 4, there is shown a solid preparation injector embodying the present invention, that comprises solid needle member 1 and protective cylindrical member 3 slidably mounted on needle member 1.

As best shown in FIG. 3, solid needle member 1 has acute tip 1a and is provided at its front part 1c with recess 1b for receiving one or more solid preparations. Front part 1c and needle body 1d are integrally bridged by fine rodlike supporting portion 1e to form a preparation chamber between supporting portion 1d and cylindrical member 3 when cylindrical member 3 is in its working position. Although recess 1b may be formed at any portion of the needle member, it is preferred to form recess 1b at a position close to tip 1a in consideration of administrating properties of the injector. Solid needle member 1 is also provided at its rear part with guide projection 1f extending parallel to its axis from its rear end toward the tip. Solid needle member 1 is made of stainless steel and has a diameter ranging from 0.5 to 3 mm and a length of 30 to 150 mm.

As best shown in FIG. 3, cylindrical member 3 is provided at its rear part with guide slit 3b which extends from the rear end of cylindrical member 3 in the direction parallel to its axis and is adapted to be guided by guide projection 1f when cylinder 3 is moved backward from its working position. Tip end 3a of the cylindrical member 3 is tapered to allow the cylindrical member to be inserted smoothly into the skin together with needle member 1.

Cylindrical member 3 may be made of any material which ensures that no interaction takes place between solid medicines and the cylindrical member 3, but it is preferred to use a transparent material. The transparent material includes, without being limited to, fluorine plastics.

Cylindrical member 3 is so designed that it may be slidably mounted on solid needle member 1 and moved in its axial direction from its working position (FIG. 1) to its resting position (FIG. 2) or vice versa to close recess 1b of needle member 1 at its working position and to open recess 1b at its resting position. Cylindrical member 3 generally has an inside diameter ranging from 0.5 to 3 mm, an outside diameter ranging from 0.6 to 5 mm, and a length of 20 to 150 mm. Preferably, cylindrical member 3 has a thickness as thin as possible to minimize a shock caused by inserting it into the body.

The solid preparations are generally composed of active ingredients and a biologically compatible carrier. Any type of active ingredients and carriers may be used alone or in combination with other ingredients or carriers. Solid preparation 2 may have any shape such as, for example, rodlike shapes, needle shapes, globular shapes, disks, granular shapes, and the like. For rodlike solid preparations, a preferred diameter ranges from 0.25 to 2.5 mm and the length is 3.0 to 50 mm. For globular solid preparations, a preferred diameter ranges from 0.25 to 2.5 mm.

In use, one or more solid preparations are administered to the patient in the following manner. If a solid preparation injector is packed aseptically and separately from solid preparations, hollow cylindrical member 3 is firstly moved backward to its resting position to open recess 1b of needle member 1, and one or more solid preparations are loaded into recess 1b from the side of needle member 1. Cylindrical member 3 is then moved forward to close recess 1b. However, these operations are not necessary if a solid preparation injector is packed aseptically together with one or more solid preparations which are previously loaded thereinto.

Tip 1a of needle member 1 is inserted into the human organism to be treated up to a suitable depth as shown in FIG. 4a and then cylindrical member 3 is moved backward under guide of projection 1f of needle member 1 to its resting position to open recess 1b of needle member 1. If necessary, cylindrical member 3 is turned around its axis to stand its slit and projection 1f of needle member 1 in a row before its backward movement.

Figure 4B:
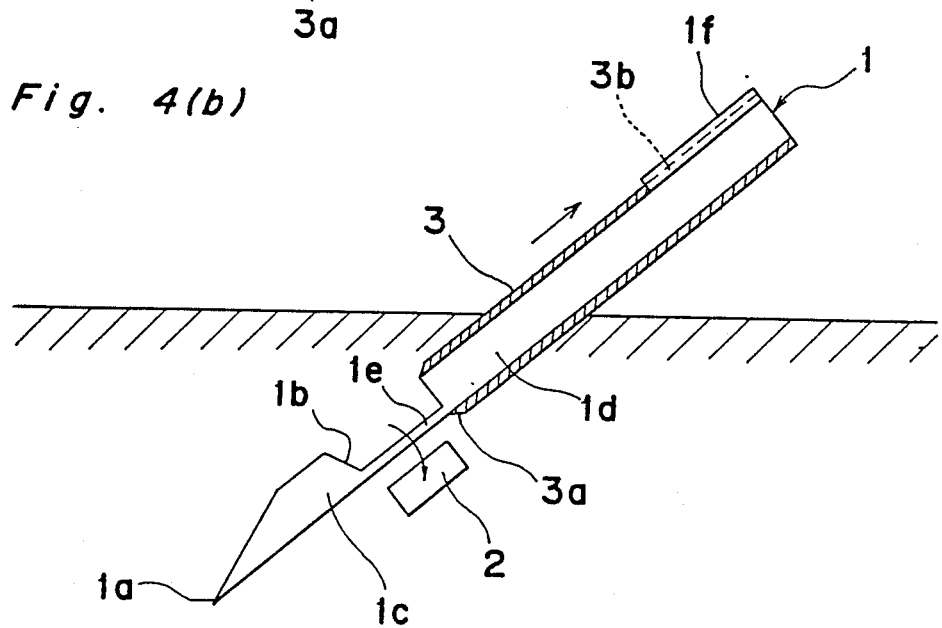

As soon as cylindrical member 3 is reached to its resting position, solid preparation 2 falls down from recess 1b and is administered to the body as shown in FIG. 4b since recess 1b of needle member 1 is opened in its circumferential direction. Then, needle member 1 is pulled up from the body. In the resting position of cylindrical member 3, if necessary, the injector is turned as a whole about its axis by a certain degree, so that solid preparation 2 held in recess 1b falls down therefrom and is administered to the body.

In the solid preparation injector of the above embodiment, the solid or semisolid preparations are held in the preparation chamber on the front part of the needle member and directly administered to the body therefrom, thus making it possible to perform implantation of the preparations without use of a plunger. Also, the preparations are administered directly from the chamber of the needle member without passing through the needle member, thus making it possible to prevent the preparations from deformation due to friction with the needle member. The number of solid preparations to be administered may be determined by size of the chamber, thus making it possible to administer two or more preparations at one time.

Figure 5:
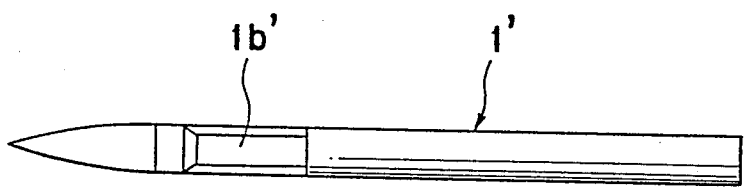
FIG. 5 is a plan view showing another form of a needle body of a solid preparation injector according to the present invention.
Figure 6:
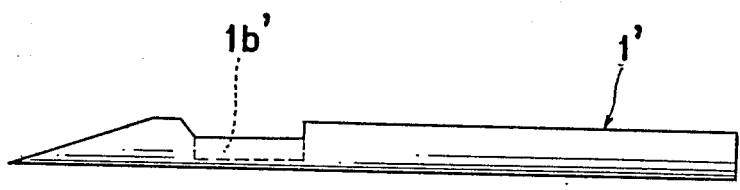
FIG. 6 is a side view of the needle member of FIG. 5.

Recess 1b of needle member 1 may be formed in any shape which makes it possible to receive one or more solid preparations from the side of the needle. For example, as shown in FIGS. 5 and 6, needle member 1' may have recess 1b' which opens upwardly and communicates with the cut portion of needle member 1'. In this case, the solid preparation is held only by recess 1b' under stable conditions. In use, it is required to turn needle member 1' by a certain angle to release the solid preparation from the recess 1b' after inserting the needle member into the body.

The bridging portion 1e of needle member 1 may have any cross section such as, for example, of circular (FIG. 7a), triangular (FIG. 7b), frustum-shaped (FIG. 7c), oval shaped, U-shaped or the like. The cross section of bridging portion 1e is determined in accordance with the shape of the solid preparation to be administered to improve administration property of the injector.

Figure 8:
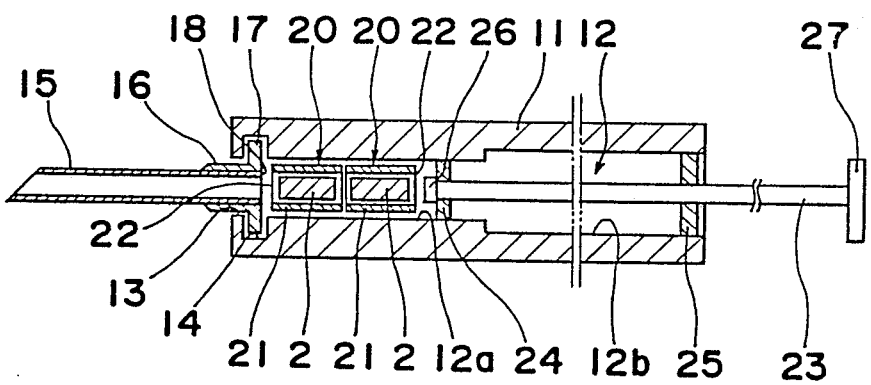
FIG. 8 is a cross section of a solid preparation injector showing another embodiment of the present invention.
Figure 9:
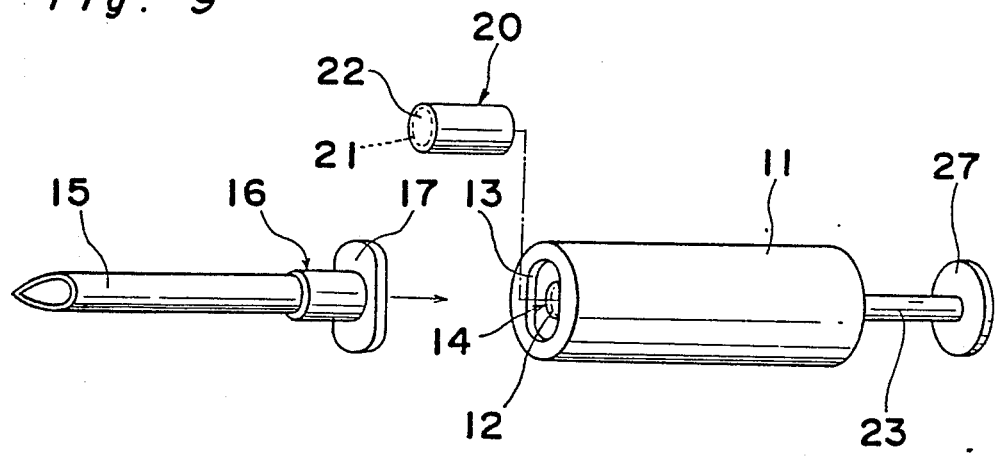
FIG. 9 is an exploded perspective view of the solid preparation injector of FIG. 8.
Figure 10:
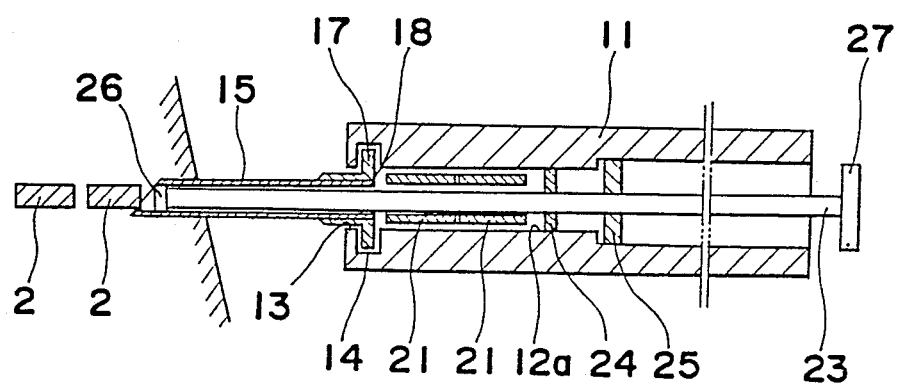
FIG. 10 is a cross section of the solid preparation injector of FIG. 8, showing solid preparations being administered under the skin of the human body.

FIGS. 8 to 10 show another form of a solid preparation injector embodying the present invention, which comprises a cylindrical body 11, a hollow needle member 15 and plunger 23, all of which have a common axis.

Cylindrical member 11 is provided with stepped-hole 12, of which front hole 12a has a diameter smaller than that of rear hole 12b and forms a capsule loading chamber into which one or more protective capsules 20 (in the drawing, two capsules) are loaded in a row. At the front end of cylindrical member 11 there is provided oblong opening 13 communicated with stepped-hole 12 through disk-like hole 14 which is formed between opening 13 and capsule chamber 12a and has a diameter larger than that of major axis of the opening 13. The longer the small-sized hole 12a of cylindrical member 11, the greater the number of the protective capsules to be loaded in the injector, thus making it possible to administer the solid preparations suitable for the purpose of treatment to the body at the same time. Cylindrical member 11 is generally designed so that it has a length of 20 to 200 mm.

Hollow needle member 15 has a form sharp at its front part and is provided at its rear end with fixing member 16 with oblong flange 17, as best shown in FIG. 9. Needle member 15 is removably mounted in the front part of cylindrical member 11 by inserting oblong flange 17 into disk-like hole 14 of cylindrical member 11 through its opening 13 and then turning needle member 15 by a certain angle. When needle member 15 is attached to cylindrical member 11, needle member 15 is arranged in a row and communicated at its rear end with capsule chamber 12a. Needle member 15 has an inside diameter smaller than the outside diameter of capsule 20 so that its rear end 18 serves as a stopper for the capsules when injecting solid preparations from the capsule into the body. Needle member 15 is generally designed so that it has an inside diameter ranging from 0.5 to 3 mm and a length of 20 to 150 mm.

Solid or semisolid preparations 2 used in this embodiment are placed in protective capsules 20 each comprising a capsule body 21 sealed at its opposite ends by sealing films 22 of a biologically compatible material. Such a capsule structure prevents the preparation from exposure to the air and secession from the capsule body, thus making it possible to keep the preparation in aseptic conditions. Capsule body 21 has a relatively large outside diameter, preferably, greater than 3 mm, an inside diameter ranging from 0.5 to 3 mm, and a length ranging from 5 to 50 mm. Capsule body 21 is made of such a material that no interaction occurs between the capsule material and preparations 2 to be encapsulated.

As a material for capsule body 21, it is preferred to use a transparent material which includes, without being limited to, polyethylene, silicone, polypropylene, polytetrafluoroethylene, and other plastics. As a material for the sealing films 22, there may be used those which are a biologically compatible and easily broken material and can protect preparations effectively, such as, for example, gelatin, collagen, starch, cellulose, albumin, silicone and the like. In order to facilitate breaking of the sealing film, it is preferred to use a sealing film having a thickness as thin as possible. It is, however, possible to use a material which is not an easily broken material or a thick film as a sealing material if the film is provided at its central portion with a rift in the form of a cross, asterisk-shape or the like.

Capsule 20 may be prepared by any process, for example, a process comprising the steps of preparing a mixed solution of one or more active ingredients and one or more carrier, freeze drying the mixed solution, grinding the resultant powder, compacting the powder to form solid preparations with a desired shape such as, for example, a rodlike shape, a needle shape, a globular shape and the like, and encapsulating the solid preparations into protective capsules.

Capsule 20 may be prepared by a process comprising the steps of kneading active ingredients and a carrier with a small quantity of water or a buffered solution, forming the material into a rodlike or needle shape by a suitable molding process such as injection molding, drying and cutting the moldings to form solid preparations, and then encapsulating the solid preparations into protective capsules. Also, the capsules may be prepared by another process which comprises the steps of mixing one or more active components with a suitable polymer, curing or hardening the resultant mixture by crosslinking or thermal polymerization to prepare solid preparations, and then encapsulating the preparations.

The capsules with semisolid preparations may be prepared in any way, for example, by a process comprising the steps of kneading active ingredients and a carrier with a small quantity of water or a buffered solution, and encapsulating a suitable amount of the resultant semisolid preparation into protective capsules.

Plunger 23 is movably arranged in the cylindrical member 11 by a pair of supporting rings 24, 25 of a rubber or plastics. Front supporting member 24 is slidably mounted on plunger 23 and is slidably in contact with the inner surface of small-sized hole 12a of cylindrical member 11, while rear supporting member 25 is fixed on plunger 23 and is slidably in contact with large-sized hole 12b of cylinder 11. In the resting position, plunger 23 extends through large-sized hole 12b of cylindrical member 11 and terminates at a position behind rear end of the protective capsule 20. Mounted on the tip of plunger 23 is pushing head 26 having a diameter slightly smaller than the inside diameter of capsule body 21. Plunger 23 is also provided at its rear end with flange 27 to assist its operations. Plunger 23 is generally designed so as to have a diameter ranging from 0.5 to 3 mm and a length of 25 to 200 mm.

As a material for the plunger and cylindrical member, there may be used those such as, for example, glasses, incorrodible metals, synthetic resins such as plastics, and the like. These material may be used alone or in combination. If the plunger and cylindrical member are of an incorrodible metal or glass, they may be used repeatedly by performing sterilization. If the plunger and cylindrical member are of a synthetic resin, they are generally disposed as expendables after only one use.

In use, one or more solid or semisolid preparations 2 in the capsules 20 are administered to the patient in the following manner. Firstly, the required number of capsules 20 are taken from aseptic packages and then loaded one by one in a row into chamber 12a of cylindrical member 11 through its opening 13 and hole 14. Needle member 15 is mounted on cylindrical member 11 by lining up oblong flange 17 of needle member 15 with oblong opening 13 of cylindrical member 11, inserting the flange 17 into opening 13, and then turning needle member 11 clockwise or counterclockwise by about 90° or until it stops. If needle member 15 is previously mounted on cylindrical member 11, needle member 11 is firstly removed from cylindrical member 11 by turning needle member 15 and lifting out the same from cylindrical member 11, and then the required number of capsules 20 are loaded into chamber 12a.

The tip of needle member 15 is then inserted into the human organism to the desired depth as shown in FIG. 10, and plunger 23 is forced into cylindrical member 11 by pushing its flange 27, while fixing the cylindrical member with fingers. Pushing head 26 breaks through capsule 20 and pushes the solid or semisolid preparations 2 in needle member 15. Capsule bodies 21 is remained in chamber 12a by the rear end 18 of needle member 15. Solid preparation 2 is then administered to the body through needle member 15 together with a part of the sealing films 22. Then, needle member 15 is pulled up from the body.

The solid preparation injector of the above embodiment has the following advantages: The operations are simple and easy since the capsules are loaded into the capsule chamber of the cylindrical member through its front opening without removal of the plunger. The front loading of the capsules contributes to shorten the length of the needle member and a stroke of the plunger, thus making it possible to prevent the plunger from breaking or bending during implanting operation of solid preparations. The moved distance of the solid preparations depends on the length of needle member or the stroke of the plunger, so that the deformation of the solid preparations may be minimized. Further, the encapsulated preparations are loaded into the chamber, thus making it possible to prevent the preparations from exposure to the air, which in turn makes it possible to keep the preparations under aseptic conditions throughout the implanting operation.

Figure 11:
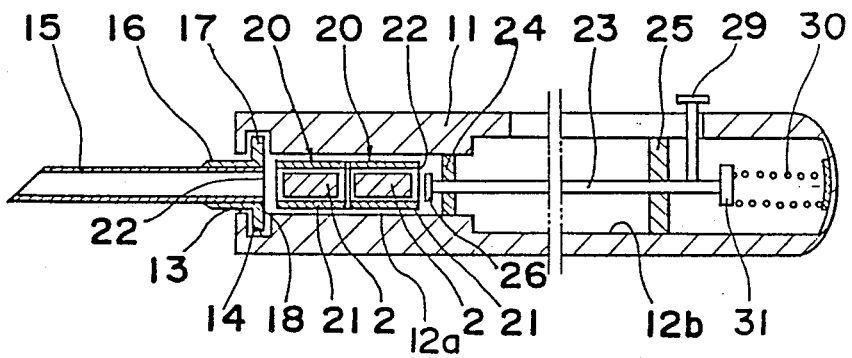
FIG. 11 is a cross section of a solid preparation injector showing another embodiment of the present invention.
Figure 12:
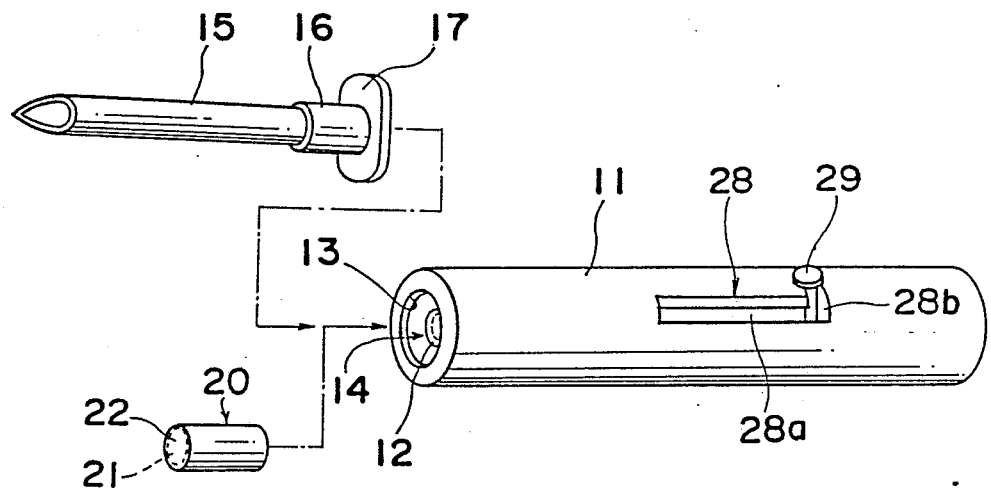
FIG. 12 is an exploded perspective view of the solid preparation injector of FIG. 11.
Figure 13:
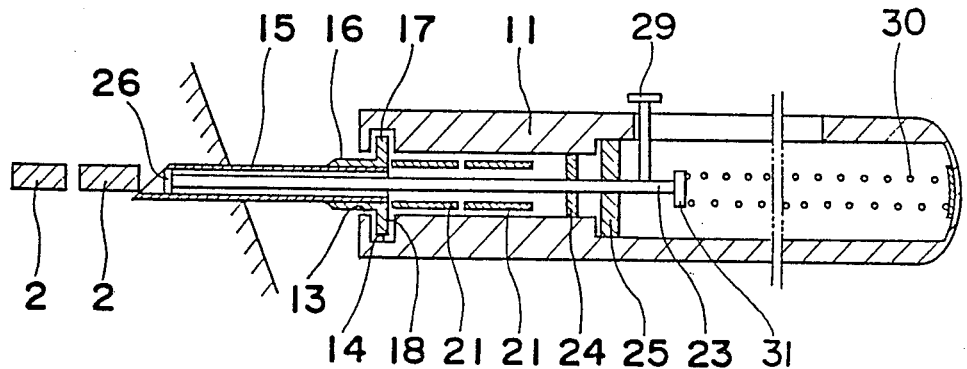
FIG. 13 is a cross section of the solid preparation injector of FIG. 12, showing solid preparations being forced out by stroke of a plunger.

Referring now to FIGS. 11 to 13, there is shown another embodiment of a solid preparation injector according to the present invention. This device has the same construction as that of the device shown in FIGS. 8 to 10 except for that it further comprises a means for forcing the plunger toward the front end of needle member 15, and a means for changing the position of a pushing head 26 of plunger 23 from the resting position close to the rear end of capsule chamber 12a to the working position close to the tip of needle member 15 or vice versa.

In this embodiment, the whole of plunger 23 is housed in stepped-hole 12 of cylindrical member 11 and is forced toward front end of the needle member 15 under the influence of spring 30 arranged between the rear ends of cylindrical member 11 and rear end 31 of plunger 23. Small-sized hole 12a of the stepped-hole 12 serves as the capsule chamber. Plunger 23 is provided at its rear part with plunger control lever 29 which extends in the direction perpendicular to the axis of plunger 23 and terminates at the outside of cylindrical member 11.

Cylindrical member 11 is provided with an L-shaped plunger control slit 28 through which large-sized hole 12b of cylindrical member 11 is communicated with the outside. Plunge control slit 28 is composed of guide slit 28a extending in the direction parallel to the axis of cylindrical member 11, and stopper slit 28b extending in the circumferential direction of cylindrical member 11 from the rear end of guide slit 28a. The length of guide slit 28a is so determined that it allows pushing head 26 of the plunger 23 to move from its resting position to the working position or vice versa. Thus, L-shaped plunger control slit 28 and plunger control lever 29 constitute a means for changing the position of a pushing head of the plunger from its resting position to the working position or vice versa.

In use, the injector is operated in the following manner: Firstly, plunger control lever 29 is placed in stopper slit 28b as shown in FIG. 12 and then the required number of capsules are loaded one by one into capsule chamber 12a of cylindrical member 11 through its opening 13 and hole 14. Hollow needle member 15 is then mounted on cylindrical member 11 by lining up its oblong flange 17 with the opening 13 of cylindrical member 11, inserting the flange 17 into hole 14 through opening 13, and then turning needle member 15 clockwise or counterclockwise by about 90° or until it stops.

After inserting needle member 15 into the body as shown in FIG. 13, plunger control lever 29 is released from stopper slit 28b by turning it counterclockwise. Thus, plunger 23 is forced toward the tip of the needle member 15 under the influence of spring 30, so that pushing head 26 of the plunger 23 enters into capsule 20 through sealing film 22 and pushes the preparations into needle 15. The capsule bodies 21 are retained in capsule chamber 12a since they hit rear end 18 of needle member 15 and are stopped from the movement. Solid preparation 2 is administered to the body through needle member 15. In this case, a part of the broken sealing films 22 are pushed into needle member 15 and implanted into the body. Then, needle member 15 is pulled up from the body.

The device of this embodiment, possesses the same advantages as those of the device shown in FIGS. 8 to 10.

EXPERIMENT 1

A column-shaped solid matter of silicone (diameter: 1.0 mm, length: 10 mm) is used as a solid preparation and administered to a mouse in the following manner. There is prepared a solid preparation administering device having a construction shown as in FIGS. 1 to 3, that comprises solid needle 1 of stainless steel (diameter: 1.5 mm, length: 70 mm), and a protective cylindrical body (inside diameter: 1.5 mm, outside diameter: 2.0, length: 40 mm) of fluoroplastics. Recess 1b (length: 12 mm) was formed apart from the tip of the needle member by 10 mm.

Figures 7A, 7B, 7C:
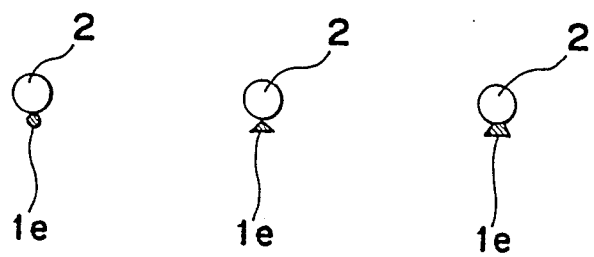
FIGS. 7a, 7b, and 7c are cross sections showing various forms of a supporting portion of a needle member with a solid preparation being placed thereon.

The column-shaped solid matter is put on recess 1b as shown in FIG. 7c and held by cylindrical member. The tip end needle member 1 is inserted under the skin of regions of back of a mouse. After sliding cylindrical member 3 toward the rear end of the needle member 1, needle member 1 is pulled out from the mouse. It has been observed that the solid preparation has fallen off from recess 1b and left under the skin of the mouse. This means that the solid preparation 2 can be administered to the body with ease and in a simple.

What is claimed is:

1. A device for subcutaneously administering solid or semisolid preparations to the human body, comprising a hollow cylindrical member having a stepped hole which is longitudinal to the cylindrical member of which the front portion that is positioned at the proximal end of the cylindrical member has a diameter smaller than that of the rear portion which is positioned at the distal end of the cylindrical member to form a capsule loading chamber, a plunger slidably mounted in said cylindrical member, and a hollow needle member removably mounted on the proximal end of said cylindrical member, said cylindrical member being provided at its proximal end with an oblong opening for attachment of said needle member and for loading of one or more capsules containing solid or semisolid preparations, said oblong opening being communicated with said chamber through a disk-like hole formed therebetween, said hollow needle member having an inside diameter smaller than the outside diameter of the capsule to form a stopper for a capsule and being provided at its rear end with a fixing member having an oblong flange insertable in the disk like hole through said oblong opening.

2. The device according to claim 1 wherein said plunger is provided with a pair of supporting rings, one of said supporting ring being fixedly mounted on the plunger and being slidable in the large sized hole of the cylindrical member, while the other being slidably mounted on the plunger.

3. The device according to claim 1 wherein the capsule loading chamber of the cylindrical member is so designed that two or more capsules are capable of being loaded therein in a row along the axis of the cylindrical member.

4. The device according to claim 3, having a capsule loaded in the capsule chamber comprising a hollow cylindrical capsule body containing a solid or semisolid preparations and being sealed at both ends with sealing films of a biologically compatible material.

5. The device according to claim 4, wherein the capsule body is comprised of polyethylene, silicone, polypropylene or polytetrafluoroethylene.

6. The device according to claim 4, wherein the biologically compatible material is gelatin, collagen, starch, cellulose, albumin or silicone.

* * * * *